(12) United States Patent
Nakamura et al.

(10) Patent No.: US 8,072,229 B2
(45) Date of Patent: Dec. 6, 2011

(54) FUEL PROPERTY SENSOR AND FUEL TANK ASSEMBLY

(75) Inventors: Hiroshi Nakamura, Nishio (JP); Akikazu Uchida, Kariya (JP)

(73) Assignee: Denso Corporation, Kariya (JP)

( * ) Notice: Subject to any disclaimer, the term of this patent is extended or adjusted under 35 U.S.C. 154(b) by 242 days.

(21) Appl. No.: 12/357,768

(22) Filed: Jan. 22, 2009

(65) Prior Publication Data

US 2009/0193873 A1 Aug. 6, 2009

(30) Foreign Application Priority Data

Jan. 31, 2008 (JP) ................................. 2008-020189

(51) Int. Cl.
*G01R 27/26* (2006.01)
(52) U.S. Cl. ........................................ 324/663; 324/686
(58) Field of Classification Search .................. 324/663; 123/458
See application file for complete search history.

(56) References Cited

U.S. PATENT DOCUMENTS

| | | | | |
|---|---|---|---|---|
| 4,479,116 A | * | 10/1984 | Kobayashi | ..................... 340/620 |
| 5,454,697 A | | 10/1995 | Nakanishi | |
| 6,431,147 B1 | * | 8/2002 | Hiraiwa et al. | ................ 123/458 |
| 6,566,892 B2 | * | 5/2003 | Schaefer et al. | ............... 324/663 |
| 7,536,989 B2 | * | 5/2009 | Tomoyuki et al. | ......... 123/198 E |
| 2005/0100461 A1 | | 5/2005 | Izutani et al. | |
| 2005/0201670 A1 | | 9/2005 | Uchiyama | |
| 2006/0042378 A1 | * | 3/2006 | Tanaka et al. | .................... 73/305 |
| 2009/0008250 A1 | * | 1/2009 | Hartl | .............................. 204/409 |

FOREIGN PATENT DOCUMENTS

| | | |
|---|---|---|
| JP | 62-035088 | 2/1987 |
| JP | S64-53957 A * | 4/1989 |
| JP | U-S64-53957 | 4/1989 |
| JP | U-H01-148854 | 10/1989 |

OTHER PUBLICATIONS

Japanese Office Action dated Oct. 6, 2009, issued in corresponding Japanese Application No. 2008-020189, with English translation.

* cited by examiner

*Primary Examiner* — Timothy J Dole

(74) *Attorney, Agent, or Firm* — Nixon & Vanderhye, PC

(57) ABSTRACT

A fuel property sensor, which is installed to a fuel tank of a fuel tank assembly, senses a property of fuel at the fuel tank. First and second electrodes of the fuel property sensor are made of an electrically conductive material and are exposed in a fuel flow passage in a housing of the fuel property sensor such that the first and second electrodes are generally parallel to a flow direction of fuel in the fuel flow passage and are spaced from each other by a predetermined distance. The fuel property sensor determines the property of the fuel based on a capacitance, which is generated between the first electrode and the second electrode.

17 Claims, 3 Drawing Sheets

FUEL PROPERTY SENSOR AND FUEL TANK ASSEMBLY

CROSS REFERENCE TO RELATED APPLICATION

This application is based on and incorporates herein by reference Japanese Patent Application No. 2008-20189 filed on Jan. 31, 2008.

BACKGROUND OF THE INVENTION

1. Field of the Invention

The present invention relates to a fuel property sensor that senses a property of fuel at a fuel tank and a fuel tank assembly having the same.

2. Description of Related Art

For example, Japanese Unexamined Utility Model Publication No. S64-53957A teaches a fuel property sensor, which is connected to a middle of a fuel pipe line in a fuel tank of a fuel tank assembly and includes two electrically conductive members exposed in fuel in the fuel pipe line. A controller applies a DC current between the two electrically conductive members and determines an ethanol concentration in the fuel based on the amount of conducted current between the two electrically conductive members.

Furthermore, Japanese Unexamined Utility Model Publication No. H01-148854A teaches another fuel property sensor that includes two cylindrical tubular bodies, which are made of an electrically conductive material and are coaxially placed in a delivery pipe made of a dielectric material while the two cylindrical tubular bodies are electrically insulated from each other. Fuel flows through a gap between the two cylindrical tubular bodies.

In the case of the fuel property sensor recited in Japanese Unexamined Utility Model Publication No. S64-53957A, since the fuel property sensor is placed in the fuel pipe line, two pipe connections are provided at opposed ends of the fuel property sensor. Thus, the number of pipe connections in the middle of the fuel pipe line is increased, and thereby the number of assembling steps is also disadvantageously increased. In the case of the fuel property sensor recited in Japanese Unexamined Utility Model Publication No. H01-148854A, the fuel property sensor is placed in the delivery pipe, so that the number of pipe connections is not increased. However, the delivery pipe is installed to the engine in such a manner that the longitudinal direction of the delivery pipe is parallel to the horizontal direction. Thus, the two cylindrical tubular bodies of the fuel property sensor are placed such that the axial direction of the two cylindrical tubular bodies is placed parallel to the horizontal direction. Thus, foreign contaminants (foreign objects), which are contained in the fuel, tend to be held in the gap between the two cylindrical tubular bodies. Thereby, the fuel property measurement accuracy of the fuel property sensor may possibly be deteriorated.

The present invention addresses the above disadvantages.

According to the present invention, there is provided a fuel property sensor that senses a property of fuel at a fuel tank, which has a tank main body and a flange fixed to the tank main body to close an opening hole of the tank main body. The fuel property sensor includes a housing and first and second electrodes. The housing defines a fuel flow passage and is installed to the flange. The fuel flow passage of the housing communicates between an inside and an outside of the tank main body to conduct the fuel therethrough. The first and second electrodes are made of an electrically conducive material and are exposed in the fuel flow passage in the housing such that the first and second electrodes extend generally parallel to a flow direction of the fuel in the fuel flow passage and are spaced from each other by a predetermined distance. The fuel property sensor determines the property of the fuel based on a capacitance, which is generated between the first electrode and the second electrode.

One end of the fuel flow passage of the housing is placed in the inside of the fuel tank, and the other end of the fuel flow passage is placed at the outside of the fuel tank. A fuel pipe line is connected to the other end of the fuel flow passage. A fuel path of the flange, which is originally present regardless of whether the fuel property sensor is provided or not, is used as the fuel flow passage of the housing (the constituent part of the fuel property sensor). In this way, the fuel property sensor can be provided without increasing the number of pipe connections in the fuel pipe line (fuel pathway).

Normally, the fuel pipe line, which supplies the fuel to the engine, is connected to the other end (the fuel tank outside end) of the fuel flow passage of the housing. In order to protect the connection between the fuel path (the fuel flow passage of the housing) and the fuel pipe line as well as the downstream side portion of the fuel pipe line located on the downstream side of this connection from, for example, stones scattered or bounced from the road surface, the flange is provided on the upper side of the fuel tank, which is placed at the upper side upon installation of the fuel tank to the vehicle. Thus, the flow direction of the fuel in the fuel flow passage of the fuel property sensor generally coincides with the top-to-bottom direction (the vertical direction) of the vehicle. Thereby, the axial direction of the first and second electrodes also generally coincides with the top-to-bottom direction of the vehicle. Therefore, even when the foreign contaminant (foreign object) is introduced between the first electrode and the second electrode, it is possible to limit the long time presence of the foreign contaminant therein by the action of the gravity.

According to the present invention, there is also provided a fuel tank assembly, which includes the fuel tank and the above fuel property sensor.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF THE INVENTION

Various embodiments of the present invention will be described with reference to the accompanying drawings.

First Embodiment

Figure 1:
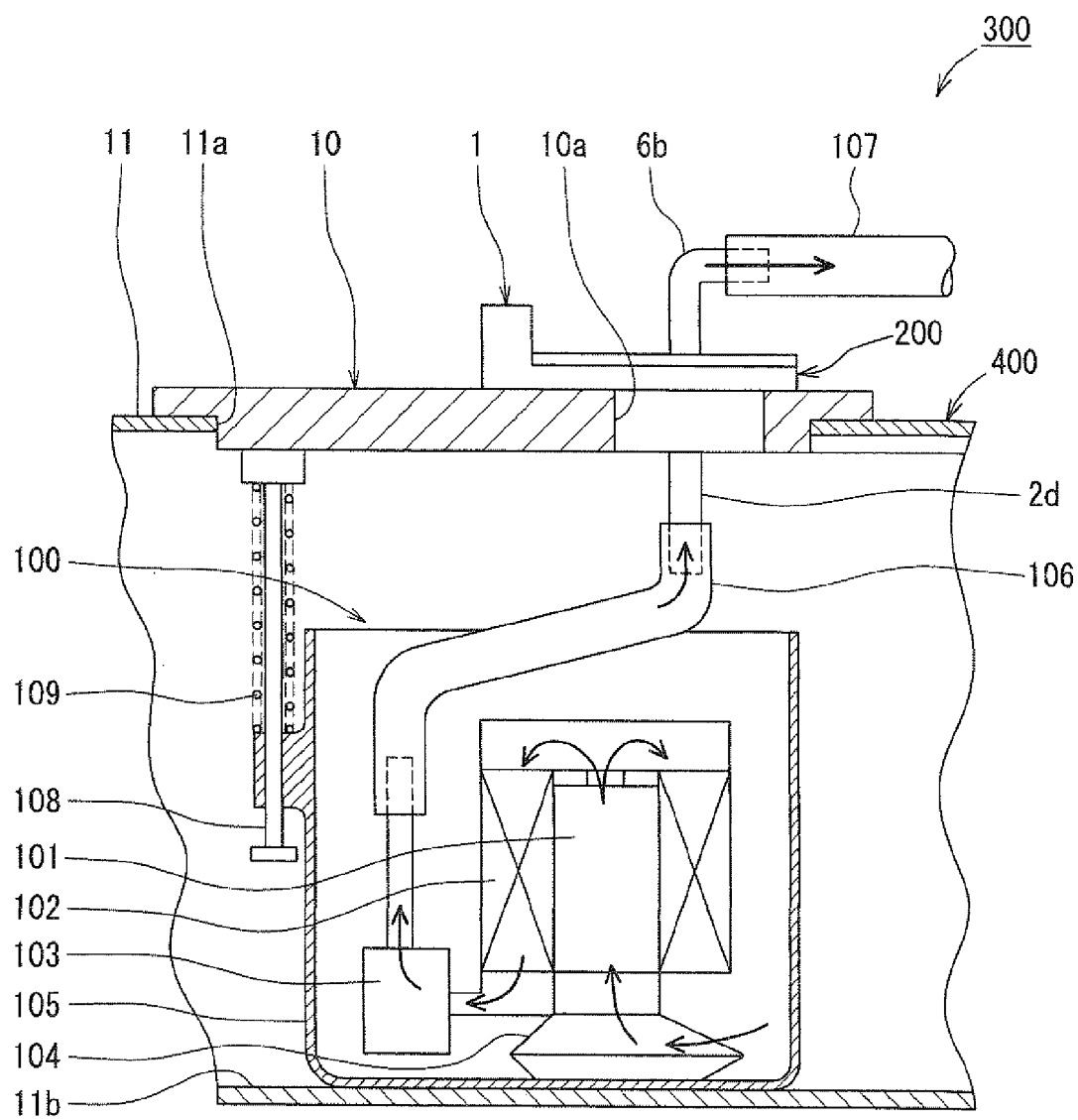
FIG. 1 is a partial cross sectional view of a fuel tank, to which a fuel property sensor according to a first embodiment of the present invention, is installed.

FIG. 1 shows a fuel tank assembly 300 according to a first embodiment of the present invention. The fuel tank assembly 300 includes a fuel tank 400 and a fuel property sensor 1. A tank main body 11 of the fuel tank 400 stores fuel that is supplied to an internal combustion engine (not shown) to drive the same. The fuel property sensor 1 is installed to a flange 10 of the fuel tank 400, which is fixed to the tank main body 11 to close an opening hole 11a that is formed in a top surface of the tank main body 11. The flange 10 holds a pump module 100 through a guide rod 108 and a coil spring 109. In the pump module 100, a fuel pump 101, a fuel filter 102, a pressure regulator 103 and a suction filter 104 are received in an inner tank 105, which has a generally cylindrical cup shaped body that has a peripheral wall and a bottom wall. As indicated by arrows in FIG. 1, the fuel is drawn into the fuel pump 101 through the suction filter 104. Then, the fuel, which is discharged from the fuel pump 101, passes through the fuel filter 102 and is supplied to the pressure regulator 103, at which the pressure of the fuel is regulated to a predetermined pressure. Thereafter, the fuel is guided to the fuel property sensor 1, which is fixed to the flange 10, through a connection pipe 106. The fuel property sensor 1 also serves as a fuel path, which communicates between the inside and the outside of the tank main body 11. The fuel, which is outputted to the outside of the tank main body 11 by passing through the fuel property sensor 1, is supplied to the engine through a connection pipe 107 of the fuel pipe line. When the flange 10 is fixed to the tank main body 11, the coil spring 109 is placed in a compressed state. Due to the resilient deformation of the coil spring 109, the pump module 100 is urged downward in FIG. 1 toward a bottom surface 11b of the tank main body 11. In this way, the pump module 100 is always placed at the lowest location in the tank main body 11. Thus, the fuel in the tank main body 11 can be effectively supplied to the engine (not shown) even when the fuel level in the tank main body 11 is relatively low.

In the present embodiment, the fuel, which is stored in the tank main body 11 of the fuel tank 400 equipped with the fuel property sensor 1, is a mixture fluid of gasoline and alcohol (more specifically, ethanol). Types of fuels, which can be supplied at gas stations, may include 100% gasoline, which does not include any ethanol, besides the mixture fluid of gasoline and ethanol, in which the ethanol concentration is adjusted to a predetermined value. Thus, the ethanol concentration of the fuel, which is stored in the fuel tank, may vary over a wide range. In order to operate the engine with such a fuel in such a manner that the operational state of the engine is always kept in the appropriate state by, for example, minimizing the noxious component quantity in the exhaust gas while generating a desired torque of the engine, the fuel property, specifically the ethanol concentration in the fuel, needs to be measured, and the control parameters of the engine (e.g., the fuel injection quantity, the fuel injection timing) need to be controlled in an appropriate manner based on the measured fuel property. The fuel property sensor 1 is used for this purpose.

Next, the structure of the fuel property sensor 1 will be described.

Figure 2:
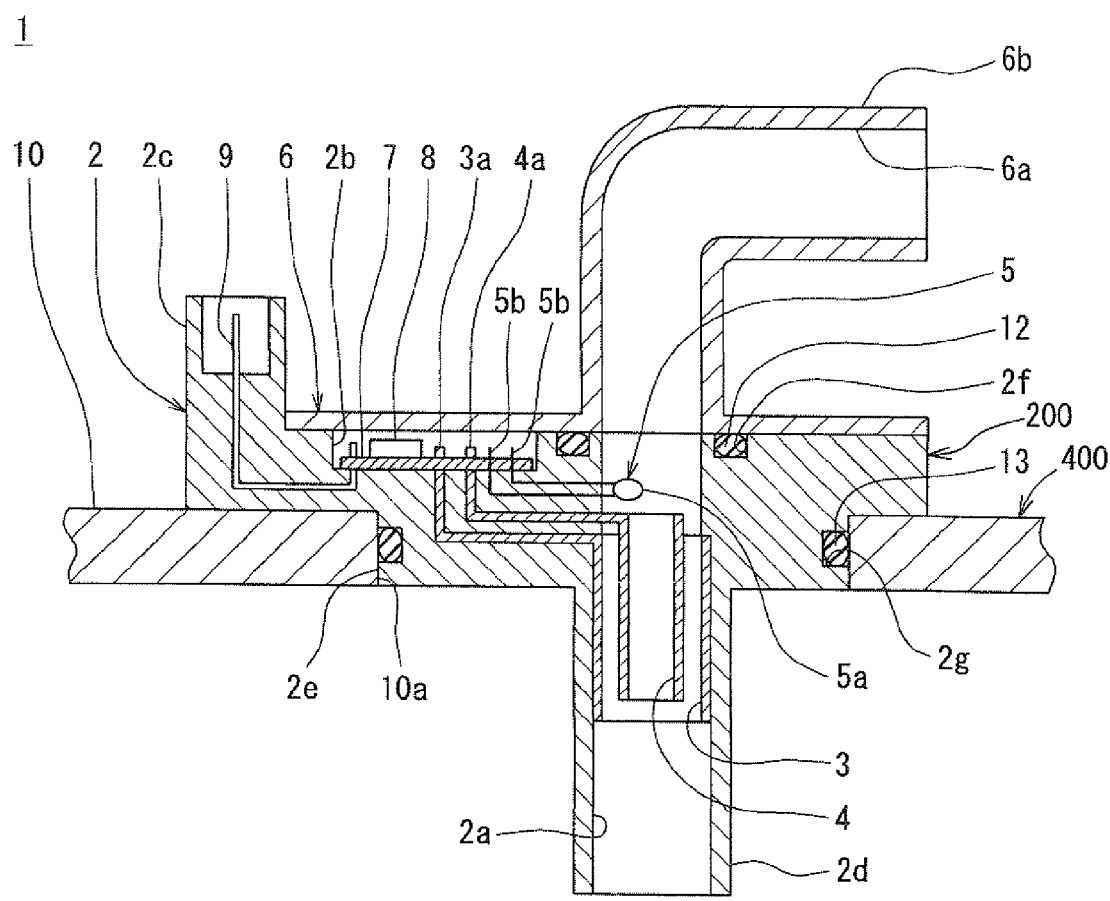
FIG. 2 is a cross sectional view of the fuel property sensor of the first embodiment.

As shown in FIG. 2, the fuel property sensor 1 includes a housing 200, a first electrode 3, a second electrode 4 and a printed circuit board 7. The housing 200 includes a housing main body 2 and a cover 6. The first electrode 3 is configured into a generally cylindrical tubular body. The second electrode 4 is configured into a generally cylindrical tubular body having a smaller diameter than that of the first electrode 3. The first and second electrodes 3, 4 are coaxial to one another and are placed in a fuel flow passage 2a in the housing main body 2. The cover 6 is installed to the housing main body 2 at the outside of the tank main body 11 and includes an outlet for outputting the fuel from the tank main body 11. The printed circuit board 7 forms an electric circuit, which measures and determines the fuel property.

The housing main body 2 is made of, for example, a resin material. The resin material is selected to be one, which is dielectric and is stable even upon contact with the gasoline and the ethanol in the case of the fuel property sensor 1 of the first embodiment. As shown in FIG. 2, the housing main body 2 includes the fuel flow passage 2a, a receiving chamber 2b, a connector 2c, a pipe 2d and a guide 2e. The fuel flow passage 2a conducts the fuel. The receiving chamber 2b receives the printed circuit board 7, which will be described below in detail. The connector 2c is adapted to be electrically connected to an external electric circuit and thereby to establish an electrical connection between the fuel property sensor 1 and the external electric circuit. The pipe 2d defines the fuel flow passage 2a therein and is placed in the inside of the tank main body 11 to form a fuel inlet of the fuel property sensor 1, which is pumped from the fuel pump 101. At the time of fixing the fuel property sensor 1 to the flange 10, the guide 2e is engaged with an opening hole 10a of the flange 10 to place the fuel property sensor 1 in position relative to the flange 10. The upper side of FIG. 2 corresponds to an upper side of the fuel property sensor 1 upon installation of the fuel tank 400, which is provided with the fuel property sensor 1, to the vehicle. Furthermore, the upper side of the flange 10 in FIG. 2 is the outside of the tank main body 11, and the lower side of the flange 10 in FIG. 2 is the inside of the tank main body 11. In the fuel flow passage 2a, the fuel flows from the lower side to the upper side in FIG. 2.

The first electrode 3 and the second electrode 4, which are respectively made of an electrically conductive material, are placed in the fuel flow passage 2a of the housing main body 2. The first electrode 3 and the second electrode 4 are configured into the cylindrical shapes and are placed coaxial to each other. Specifically, an outer peripheral surface of the first electrode 3 is fixed to the inner wall of the fuel flow passage 2a, and the second electrode 4 is placed radially inward of the first electrode 3. The first electrode 3 and the second electrode 4 are made of a material (e.g., a stainless steel plate), which is electrically conductive and is corrosion resistant against the fuel, specifically the gasoline and the ethanol. For instance, the stainless steel plates may be respectively processed to form the first and second electrodes 3, 4 through, for example, press working. A first lead 3a and a second lead 4a project radially outward from one axial ends, respectively of the first and second electrodes 3, 4, which are located on the common axial side of the first and second electrodes 3, 4. The first and second leads 3a, 4a are electrically connected to the printed circuit board 7, which is the electric circuit described below in detail, so that the first and second electrodes 3, 4 are electrically connected to the printed circuit board 7. That is, the first electrode 3 is electrically connected to the printed circuit board 7 through the first lead 3a, and the second electrode 4 is electrically connected to the printed circuit board 7 through the second lead 4a. The first and second electrodes 3, 4 are securely held through insert molding in the housing main body 2, which is made of the resin material. Each lead 3a, 4a may be formed integrally with the corresponding electrode 3, 4. Alternatively, each lead 3a, 4a may be formed separately from the corresponding electrode 3, 4 and may be thereafter joined to or connected to the corresponding electrode 3, 4. A capacitance, which is generated between the first electrode 3 and the second electrode 4, is computed, i.e., is determined at the printed circuit board 7 based on a voltage between the first electrode 3 and the second electrode 4.

As shown in FIG. 2, a thermistor 5 is placed in the fuel flow passage 2a to measure the fuel temperature. A temperature sensing element 5a of the thermistor 5 is exposed in the fuel flow passage 2a on the downstream side of the first and second electrodes 3, 4, and leads 5b of the thermistor 5 are electrically connected to the printed circuit board 7. Similar to the first and second electrodes 3, 4, the thermistor 5 is fixed in the housing main body 2 through the insert molding. The temperature, which is measured with the thermistor 5, is monitored by the printed circuit board 7 where the measured value of the capacitance is temperature compensated based on the measured temperature.

The housing main body 2 includes the connector 2c to connect the fuel property sensor 1 to the external electric circuit. As shown in FIG. 2, terminals 9, each of which is made of an electrically conductive metal, are provided in the connector 2c. One end of each terminal 9 is placed in the connector 2c, and the other end of each terminal 9 is connected to the printed circuit board 7. Although only one of the terminals 9 is shown in FIG. 2, the multiple terminals 9 are actually provided. Similar to the first and second electrodes 3, 4, the terminals 9 are fixed in the housing main body 2 through the insert molding.

The cover 6 is fixed to the housing main body 2 at the outside end portion of the fuel flow passage 2a of the housing main body 2, which is located at the outside of the tank main body 11. The cover 6 is made of the resin material, which is the same as that of the housing main body 2. The cover 6 includes a fuel flow passage 6a, which serves as an extension of the fuel flow passage 2a of the housing main body 2 and is smoothly connected to the fuel flow passage 2a. The cover 6 has the pipe 6b, which defines the fuel flow passage 6a therein. The pipe 6b is located at the outside of the tank main body 11 and forms the fuel outlet of the fuel property sensor 1. As shown in FIG. 2, at the connection between the fuel flow passage 2a and the fuel flow passage 6a, an O-ring 12 is fitted to an annular groove 2f of the housing main body 2 to maintain the fluid-tightness at the connection between the fuel flow passage 2a and the fuel flow passage 6a (i.e., between the housing main body 2 and the pipe 6b of the cover 6). Here, the fuel flow passage 2a and the fuel flow passage 6a cooperate together to form a fuel flow passage of the housing 200. As shown in FIG. 2, the cover 6 gas-tightly, i.e., fluid-tightly covers the receiving chamber 2b of the housing main body 2. In this way, the printed circuit board 7 in the receiving chamber 2b is protected from foreign contaminants, water, fuel or the like.

As shown in FIG. 2, at the engaging portion between the guide 2e of the housing main body 2 and the opening hole 10a of the flange 10, an O-ring 13 is fitted to an annular groove 2g of the guide 2e to maintain the gas-tightness, i.e., the fluid-tightness between the housing main body 2 and the flange 10.

The printed circuit board 7 may be, for example, a glass epoxy circuit board or a ceramic circuit board. The first electrode 3, the second electrode 4 and the thermistor 5 are connected to the printed circuit board 7. Furthermore, an integrated circuit (IC) 8 and undepicted other electronic elements are installed on the printed circuit board 7 to form the electric circuit of the fuel property sensor 1. The printed circuit board 7 is connected to the external electric circuit through the connector 2c and the terminals 9.

Next, the manufacturing method of the fuel property sensor 1 according to the first embodiment will be described.

First, the housing main body 2 is made by the resin molding. At this time, the first electrode 3, the second electrode 4, the thermistor 5 and the terminals 9 are insert molded in the housing main body 2.

Next, the printed circuit board 7 is installed in the receiving chamber 2b of the housing main body 2. By this time, the electronic elements, such as the IC 8, have been already installed to the printed circuit board 7. An end portion of the first lead 3a of the first electrode 3, an end portion of the second lead 4a of the second electrode 4, end portions of the leads 5b of the thermistor 5 and end portions of the terminals 9 opposite from the connector 2c project in the inside of the receiving chamber 2b of the housing main body 2. Installation holes are formed in the printed circuit board 7 at locations, which correspond to the leads 3a, 4a, 5b and the terminals 9. Therefore, while the leads 3a, 4a, 5b and the terminals 9 are fitted into the installation holes of the printed circuit board 7, the printed circuit board 7 is set in the receiving chamber 2b. Then, the leads 3a, 4a, 5b and the terminals 9 are electrically connected to the circuit of the printed circuit board 7 through, for example, soldering.

Next, the O-ring 12 is installed to the annular groove 2f of the housing main body 2, and thereafter the cover 6 is installed to the housing main body 2. The fixation of the cover 6 to the housing main body 2 may be made through, for example, undepicted screws (e.g., self-tapping screws).

Now, the assembling of the fuel property sensor 1 is completed. While the O-ring 13 is installed in the annular groove 2g, which is formed in the guide 2e of the housing main body 2, the guide 2e is fitted into the opening hole 10a of the flange 10. Thereby the fuel property sensor 1 is installed to the flange 10. The fixation of the fuel property sensor 1 to the flange 10 is executed by, for example, screwing, bonding or the like.

Now, effects and advantages of the fuel property sensor 1 of the first embodiment will be described.

First of all, the fuel property sensor 1 of the first embodiment is fixed to the flange 10. Thus, the fuel flow passages 2a, 6a of the fuel property sensor 1 also serve as the fuel path of the fuel path member, which communicates between the inside and the outside of the tank main body 11. In other words, the structure of the fuel property sensor 1 of the first embodiment is equivalent to the structure, in which the fuel property sensor is installed to the fuel path member that is originally provided in the fuel tank. In this way, in comparison to the previously proposed fuel property sensor, which is placed in the middle of the fuel pipe that is provided in the fuel tank or that extends from the fuel tank to the engine, it is possible to reduce the number of pipe connections in the fuel pathway from the pump module outlet in the fuel tank to the engine. As a result, the fuel property sensor 1 of the first embodiment enables the reduction in the number of the pipe connections to reduce the number of pipe connection components and the number of assembling steps of the pipe connection components.

Second of all, in the fuel property sensor 1 of the first embodiment, the flange 10, to which the fuel property sensor 1 is installed, is provided to the upper surface of the tank main body 11 upon the installation of the fuel tank 400 to the vehicle. In this way, the flow direction of the fuel in the fuel flow passages 2a, 6a of the fuel property sensor 1, which serve as the fuel path member that communicates between the inside and the outside of the tank main body 11, is directed from the lower side to the upper side in the vehicle. In this way, even when the foreign contaminant (the foreign object) flows into the generally annular gap between the first electrode 3 and the second electrode 4, which are configured into the generally cylindrical tubular bodies and are coaxial to one another, the foreign contaminant is forced to move out of the gap between the first electrode 3 and the second electrode 4 by the action of the gravity. Therefore, it is possible to limit the foreign contaminant to stay in the gap between the first electrode 3 and the second electrode 4 for a long period of time. As a result, it is possible to limit the reduction in the measurement accuracy of the fuel property caused by the long time presence of the foreign contaminant in the fuel between the first electrode 3 and the second electrode 4.

Third of all, in the fuel property sensor 1 of the first embodiment, the first electrode 3 and the second electrode 4 integrally have the first lead 3a and the second lead 4a, respectively, at the one axial ends on the common side. The first lead 3a and the second lead 4a extend radially outward from the first electrode 3 and the second electrode 4 and are directly electrically connected to the printed circuit board 7. In this way, in comparison to the previously proposed fuel property sensor, in which each electrode is connected to the electric circuit through the electrically conductive element, such as the lead line, it is possible to reduce the stray capacitance, which is generated between the electrically conductive elements that connect the electrodes to the electric circuit. The stray capacitance, which is generated between the electrically conductive elements, acts as a noise in the electric circuit of the fuel property sensor. Thus, when the stray capacitance is reduced, the measurement accuracy of the fuel property sensor 1 can be improved.

Fourth of all, in the fuel property sensor 1 of the first embodiment, the first and second electrodes 3, 4 are fixed by insert molding of the first and second electrodes 3, 4 in the housing main body 2. In this way, the installation positional accuracy of the first and second electrodes 3, 4 relative to the housing main body 2, and the positional accuracy between the first electrode 3 and the second electrode 4 (i.e., the gap configuration accuracy between the first electrode 3 and the second electrode 4) are improved. As a result, the measurement accuracy of the fuel property sensor 1 can be improved. Furthermore, the number of the assembling steps of the fuel property sensor 1 can be reduced.

Second Embodiment

A fuel property sensor 1 of a second embodiment of the present invention differs from that of the first embodiment with respect to the housing 200. Specifically, in the second embodiment, the fuel flow passage is formed only by the fuel flow passage 2a of the housing main body 2 of the housing 200 in the fuel property sensor 1 while the cover 6 of the housing 200 only has the function of covering the receiving chamber 2b. In the following description, components similar to those of the first embodiment will be indicated by the same reference numerals and will not be described further.

Figure 3:
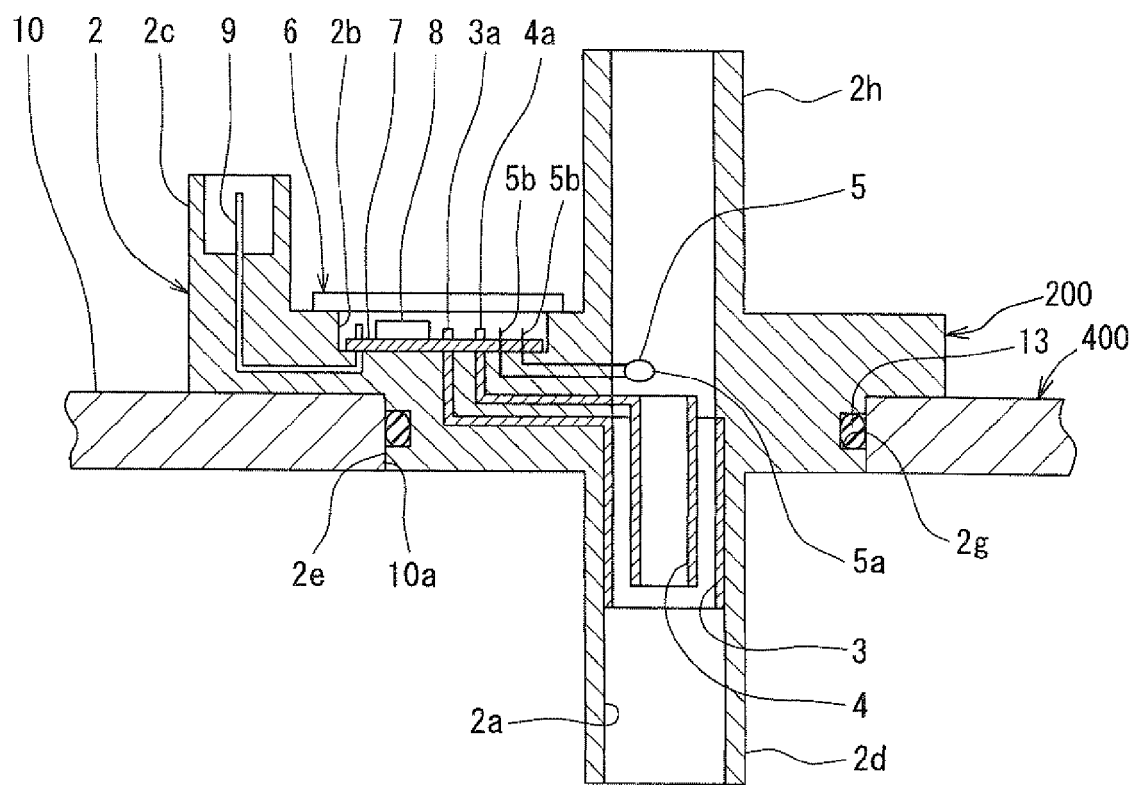
FIG. 3 is a cross sectional view of a fuel property sensor according to a second embodiment of the present invention.

As shown in FIG. 3, in the second embodiment, a pipe 2h is integrally formed in the housing main body 2 at the outside of the tank main body 11, and the fuel flow passage 2a is extended into the pipe 2h. Furthermore, as shown in FIG. 3, the cover 6 is fixed to the housing main body 2 to cover the receiving chamber 2b, which receives the printed circuit board 7.

Even in the fuel property sensor 1 of the second embodiment, the advantages similar to those of the fuel property sensor 1 of the first embodiment can be achieved.

In the first and second embodiments, the housing main body 2 of the fuel property sensor 1 and the flange 10 are formed as the separate components. Alternatively, the housing main body 2 of the housing 200 of the fuel property sensor 1 and the flange 10 may be formed integrally through, for example, resin molding.

Also, in the first and second embodiments, the subject fuel, the property of which is measured with the fuel property sensor 1, is the mixture fluid of the ethanol and the gasoline. The combination of the components of the fuel is not limited to the above combination, and any two kinds of liquids may be mixed to form the mixture fluid of the fuel. For example, the fuel may be a mixture fluid of light oil and methanol or alternatively an emulsion of heavy oil and water.

Additional advantages and modifications will readily occur to those skilled in the art. The invention in its broader terms is therefore not limited to the specific details, representative apparatus, and illustrative examples shown and described.

What is claimed is:

1. A fuel property sensor that senses a property of fuel at a fuel tank, which has a tank main body and a flange fixed to the tank main body to close an opening hole of the tank main body, the fuel property sensor comprising:
    a housing that defines a fuel flow passage and is installed to the flange, wherein the fuel flow passage of the housing communicates between an inside and an outside of the tank main body to conduct the fuel therethrough;
    first and second electrodes that are made of an electrically conductive material and are exposed in the fuel flow passage in the housing such that the first and second electrodes extend generally parallel to a flow direction of the fuel in the fuel flow passage and are spaced from each other by a predetermined distance, wherein the fuel property sensor determines the property of the fuel based on a capacitance, which is generated between the first electrode and the second electrode;
    an electric circuit that is disposed in the housing, wherein the electric circuit is electrically connected to the first and second electrodes and computes a capacitance between the first electrode and the second electrode based on a voltage between the first electrode and the second electrode;
    a first lead that is formed integrally with the first electrode in one piece and extends to the electric circuit; and
    a second lead that is formed integrally with the second electrode in one piece and extends to the electric circuit, wherein the first lead and the second lead are directly physically joined to the electric circuit to electrically connect the first and second electrodes to the electric circuit.

2. The fuel property sensor according to claim 1, wherein:
    the first lead extends outward at one axial end portion of the first electrode; and
    the second lead extends outward at one axial end portion of the second electrode.

3. The fuel property sensor according to claim 1, wherein:
    the housing extends through the flange from an inside of the fuel tank to an outside of the fuel tank to define the fuel flow passage, which extends from the inside of the fuel tank to the outside of the fuel tank;
    the housing is integrally molded in one piece from a resin material; and
    the first and second electrodes are insert molded in the housing.

4. The fuel property sensor according to claim 1, wherein the flange is fixed to a surface of the tank main body, which is placed on an upper side of the tank main body upon installation of the fuel tank to a vehicle.

5. The fuel property sensor according to claim 1, wherein the flange holds a pump module, which includes:
    a fuel pump that pumps the fuel received in the tank main body; and
    a filter that filters the fuel.

6. The fuel property sensor according to claim 1, wherein:
    the flange is molded from a resin material; and
    at least a portion of the housing is formed integrally with the flange.

7. A fuel tank assembly comprising:
a fuel tank, which has a tank main body and a flange fixed to the tank main body to close an opening hole of the tank main body; and
the fuel property sensor of claim 1.

8. The fuel tank assembly according to claim 7, wherein the flange holds a pump module, which includes:
a fuel pump that pumps the fuel received in the tank main body; and
a filter that filters the fuel.

9. The fuel property sensor according to claim 1, wherein:
the fuel property sensor senses the property of the fuel at the fuel tank of a vehicle; and
the first and second electrodes extend generally parallel to the flow direction of the fuel, which is directed from a vertically lower side to a vertically upper side of the vehicle.

10. The fuel property sensor according to claim 1, wherein the first and second electrodes are spaced from each other by the predetermined distance in a radial direction of the fuel flow passage.

11. The fuel property sensor according to claim 1, wherein the first and second electrodes extend generally parallel to an axial direction of a section of the fuel flow passage in which the first and second electrodes are exposed.

12. The fuel property sensor according to claim 1, wherein:
the first electrode has a generally cylindrical tubular body, which is exposed in the fuel flow passage and is elongated in the flow direction of the fuel;
the second electrode has a generally cylindrical tubular body, which is exposed in the fuel flow passage and is elongated in the flow direction of the fuel; and
a diameter of the generally cylindrical tubular body of the second electrode is smaller than that of the generally cylindrical tubular body of the first electrode; and
the generally cylindrical tubular body of the first electrode and the generally cylindrical tubular body of the second electrode are generally coaxial to each other.

13. The fuel property sensor according to claim 1, wherein:
the housing includes a housing main body, which is integrally molded in one piece from a resin material and forms at least a part of the fuel flow passage of the housing;
the housing main body includes a receiving chamber, in which the electric circuit is received; and
the first and second leads are fluid-tightly insert molded in the housing main body to limit intrusion of the fuel from the fuel flow passage to the receiving chamber of the housing main body along the first and second leads.

14. The fuel property sensor according to claim 13, wherein the housing main body further includes a connector, which is exposed to the outside of the fuel tank and is adapted to be electrically connected to an external electric circuit and thereby to establish an electrical connection between the electric circuit and the external electric circuit.

15. A fuel property sensor that senses a property of fuel at a fuel tank, the fuel property sensor comprising:
a housing that is installed to the fuel tank and forms a fuel flow passage, wherein a fuel inlet and a fuel outlet of the fuel flow passage of the housing are exposed in an inside and an outside, respectively, of the fuel tank to conduct the fuel from the inside to the outside of the fuel tank, and the housing includes a housing main body that is integrally molded in one piece from a resin material and forms at least a part of the fuel flow passage of the housing, which includes the fuel inlet of the housing;
first and second electrodes that are made of an electrically conductive material and are exposed in the fuel flow passage in the housing main body, wherein the fuel property sensor determines the property of the fuel based on a capacitance, which is generated between the first electrode and the second electrode;
an electric circuit that is disposed in a receiving chamber of the housing main body, wherein the electric circuit is electrically connected to the first and second electrodes and computes a capacitance between the first electrode and the second electrode based on a voltage between the first electrode and the second electrode;
a first lead that is formed integrally with the first electrode in one piece and extends to the electric circuit;
a second lead that is formed integrally with the second electrode in one piece and extends to the electric circuit, wherein the first lead and the second lead are directly physically joined to the electric circuit to electrically connect the first and second electrodes to the electric circuit; and
the first and second leads are fluid-tightly insert molded in the housing main body to limit intrusion of the fuel from the fuel flow passage into the receiving chamber of the housing main body along the first and second leads.

16. The fuel property sensor according to claim 15, wherein the housing main body is installed to or is formed integrally with a flange, which is fixed to the fuel tank to close an opening hole of the fuel tank.

17. The fuel property sensor according to claim 15, wherein the housing main body further includes a connector, which is exposed to the outside of the fuel tank and is adapted to be electrically connected to an external electric circuit, thereby to establish an electrical connection between the electric circuit and the external electric circuit.

* * * * *